© United States Patent  (10) Patent No.: US 8,062,500 B2
Sumita                       (45) Date of Patent:     Nov. 22, 2011

(54) METHOD AND APPARATUS FOR PRODUCING NEGATIVE AND POSITIVE OXIDATIVE REDUCTIVE POTENTIAL (ORP) WATER

(75) Inventor: Osao Sumita, Tokyo-to (JP)

(73) Assignee: Oculus Innovative Sciences, Inc., Petaluma, CA (US)

( * ) Notice: Subject to any disclaimer, the term of this patent is extended or adjusted under 35 U.S.C. 154(b) by 712 days.

(21) Appl. No.: 10/496,092

(22) PCT Filed: Dec. 5, 2002

(86) PCT No.: PCT/US02/38861
§ 371 (c)(1),
(2), (4) Date: May 19, 2004

(87) PCT Pub. No.: WO03/048421
PCT Pub. Date: Jun. 12, 2003

(65) Prior Publication Data
US 2005/0121334 A1    Jun. 9, 2005

(51) Int. Cl.
C25B 1/04         (2006.01)
(52) U.S. Cl. ........ 205/628; 205/742; 205/242; 205/252; 205/263
(58) Field of Classification Search .................. 204/252, 204/263, 242; 205/628, 742
See application file for complete search history.

(56) References Cited

U.S. PATENT DOCUMENTS

| | | |
|---|---|---|
| 3,066,095 A | 11/1962 | Hironas |
| 3,975,246 A | 8/1976 | Eibl et al. |
| 4,048,032 A | 9/1977 | Eibl |
| 4,121,991 A | 10/1978 | Miller et al. |

(Continued)

FOREIGN PATENT DOCUMENTS

CN    1 231 994 A    10/1999

(Continued)

OTHER PUBLICATIONS

International Search Report in PCT/US2004/043961 (Nov. 25, 2005).

(Continued)

Primary Examiner — Alexa D. Neckel
Assistant Examiner — Nicholas A. Smith
(74) Attorney, Agent, or Firm — Leydig, Voit & Mayer, Ltd.

(57) ABSTRACT

A method and apparatus for electrolytically producing oxidation reduction potential water from aqueous salt solutions for use in disinfection, sterilization, decontamination, wound cleansing. The apparatus includes an electrolysis unit having a three-compartment cell (22) comprising a cathode chamber (18), an anode chamber (16), and a saline solution chamber (20) interposed between the anode and cathode chambers. Two communicating (24, 26) membranes separate the three chambers. The center chamber includes a fluid flow inlet (21a) and outlet (21b) and contains insulative material that ensures direct voltage potential does not travel through the chamber. A supply of water flows through the cathode and anode chambers at the respective sides of the saline chamber. Saline solution flows through the center chamber, either by circulating a pre-prepared aqueous solution containing ionic species, or, alternatively, by circulating pure water or an aqueous solution of, e.g., aqueous hydrogen chloride and ammonium hydroxide, over particulate insulative material coated with a solid electrolyte. Electrical current is provided to the communicating membranes separating the chambers, thus causing an electrolytic reaction that produces both oxidative (positive) and reductive (negative) ORP water.

2 Claims, 5 Drawing Sheets

U.S. PATENT DOCUMENTS

| | | | |
|---|---|---|---|
| 4,236,992 A | 12/1980 | Themy | |
| 4,242,446 A | 12/1980 | Madappally et al. | |
| 4,296,103 A | 10/1981 | Laso | |
| 4,767,511 A | 8/1988 | Aragon | |
| 4,979,938 A | 12/1990 | Stephen et al. | |
| 5,079,010 A | 1/1992 | Natterer et al. | |
| 5,084,011 A | 1/1992 | Grady | |
| 5,244,768 A | 9/1993 | Inaba | |
| 5,271,943 A | 12/1993 | Bogart et al. | |
| 5,334,383 A | 8/1994 | Morrow | |
| 5,376,242 A | 12/1994 | Hayakawa | |
| 5,427,667 A | 6/1995 | Bakhir et al. | |
| 5,445,722 A | 8/1995 | Yamaguti et al. | |
| 5,474,662 A | 12/1995 | Miyamae | |
| 5,507,932 A | 4/1996 | Robinson | |
| 5,510,009 A | 4/1996 | Arai et al. | |
| 5,543,030 A | 8/1996 | Shiramizu et al. | |
| 5,560,816 A | 10/1996 | Robinson | |
| 5,578,022 A | 11/1996 | Scherson et al. | |
| 5,593,554 A | 1/1997 | Yamanaka et al. | |
| 5,599,438 A | 2/1997 | Shiramizu et al. | |
| 5,615,764 A | 4/1997 | Satoh | |
| 5,616,221 A | 4/1997 | Aoki et al. | |
| 5,620,587 A | 4/1997 | Nakamura | |
| 5,622,725 A | 4/1997 | Kross | |
| 5,622,848 A | 4/1997 | Morrow | |
| 5,624,535 A | 4/1997 | Tsuchikawa et al. | |
| 5,624,544 A * | 4/1997 | Deguchi et al. | 205/742 |
| 5,628,888 A | 5/1997 | Bakhir et al. | |
| 5,635,040 A | 6/1997 | Bakhir et al. | |
| 5,635,053 A | 6/1997 | Aoki et al. | |
| 5,662,625 A | 9/1997 | Westwood | |
| 5,674,365 A | 10/1997 | Sano | |
| 5,674,537 A | 10/1997 | Morrow | |
| 5,720,869 A | 2/1998 | Yamanaka et al. | |
| 5,728,274 A | 3/1998 | Kamitani et al. | |
| 5,728,287 A | 3/1998 | Hough et al. | |
| 5,731,008 A | 3/1998 | Morrow | |
| 5,736,027 A | 4/1998 | Nakamura | |
| 5,759,489 A | 6/1998 | Miura et al. | |
| 5,762,779 A | 6/1998 | Shiramizu et al. | |
| 5,783,052 A | 7/1998 | Bakhir et al. | |
| 5,792,090 A | 8/1998 | Ladin | |
| 5,798,028 A | 8/1998 | Tsuchikawa et al. | |
| 5,833,831 A | 11/1998 | Kitajima et al. | |
| 5,843,291 A | 12/1998 | Eki et al. | |
| 5,858,201 A | 1/1999 | Otsuka et al. | |
| 5,858,202 A | 1/1999 | Nakamura | |
| 5,871,623 A | 2/1999 | Dakhir et al. | |
| 5,888,357 A | 3/1999 | Mitsumori et al. | |
| 5,897,757 A | 4/1999 | Sano | |
| 5,900,257 A | 5/1999 | Breton et al. | |
| 5,902,619 A | 5/1999 | Rubow et al. | |
| 5,906,810 A | 5/1999 | Turner | |
| 5,928,488 A | 7/1999 | Newman | |
| 5,928,491 A | 7/1999 | Yu et al. | |
| 5,932,171 A | 8/1999 | Malchesky | |
| 5,938,915 A | 8/1999 | Morisawa | |
| 5,938,916 A | 8/1999 | Bryson et al. | |
| 5,944,978 A | 8/1999 | Okazaki | |
| 5,948,220 A | 9/1999 | Kamitani et al. | |
| 5,951,859 A | 9/1999 | Miura et al. | |
| 5,963,435 A | 10/1999 | Biernson | |
| 5,964,089 A | 10/1999 | Murphy et al. | |
| 5,965,009 A | 10/1999 | Shimamune et al. | |
| 5,985,110 A | 11/1999 | Bakhir et al. | |
| 5,993,639 A | 11/1999 | Miyashita et al. | |
| 5,997,717 A | 12/1999 | Miyashita et al. | |
| 6,007,686 A | 12/1999 | Welch et al. | |
| 6,007,693 A | 12/1999 | Silveri | |
| 6,007,696 A | 12/1999 | Takayasu et al. | |
| 6,033,539 A | 3/2000 | Gablenko | |
| 6,056,866 A | 5/2000 | Maeda et al. | |
| 6,059,941 A | 5/2000 | Bryson et al. | |
| 6,093,292 A | 7/2000 | Akiyama | |
| 6,106,691 A | 8/2000 | Nakamura et al. | |
| 6,117,285 A | 9/2000 | Welch et al. | |
| 6,121,317 A | 9/2000 | Wu et al. | |
| 6,126,796 A | 10/2000 | Shimamune et al. | |
| 6,126,810 A | 10/2000 | Fricker et al. | |
| 6,139,876 A | 10/2000 | Kolta | |
| 6,143,163 A | 11/2000 | Sawamoto et al. | |
| 6,149,780 A | 11/2000 | Miyake | |
| 6,171,551 B1 | 1/2001 | Malchesky et al. | |
| 6,174,419 B1 | 1/2001 | Akiyama | |
| 6,187,154 B1 | 2/2001 | Yamaguchi et al. | |
| 6,200,434 B1 | 3/2001 | Shinjo et al. | |
| 6,210,748 B1 | 4/2001 | Nagahara et al. | |
| 6,228,251 B1 | 5/2001 | Okazaki | |
| 6,231,747 B1 | 5/2001 | Fukuzuka et al. | |
| 6,231,878 B1 | 5/2001 | Komatsu et al. | |
| 6,251,259 B1 | 6/2001 | Satoh et al. | |
| 6,258,225 B1 | 7/2001 | Yamaoka | |
| 6,277,266 B1 | 8/2001 | Yamaoka | |
| 6,280,594 B1 | 8/2001 | Yamaoka | |
| 6,294,073 B1 | 9/2001 | Shirota et al. | |
| 6,296,744 B1 | 10/2001 | Djeiranishvili et al. | |
| 6,333,054 B1 | 12/2001 | Rogozinski | |
| 6,342,150 B1 | 1/2002 | Sale et al. | |
| 6,350,376 B1 | 2/2002 | Imaoka et al. | |
| 6,358,395 B1 | 3/2002 | Schorzman et al. | |
| 6,361,665 B1 | 3/2002 | Vorack | |
| 6,368,592 B1 | 4/2002 | Colton et al. | |
| 6,375,809 B1 | 4/2002 | Kato et al. | |
| 6,384,363 B1 | 5/2002 | Hayakawa et al. | |
| 6,391,169 B1 | 5/2002 | Hara et al. | |
| 6,426,066 B1 | 7/2002 | Najafi et al. | |
| 6,444,255 B2 | 9/2002 | Nagahara et al. | |
| 6,462,250 B1 | 10/2002 | Kuriyama et al. | |
| 6,464,845 B2 | 10/2002 | Shirota et al. | |
| 6,475,371 B1 | 11/2002 | Shirahata et al. | |
| 6,506,416 B1 | 1/2003 | Okauchi et al. | |
| 6,527,940 B1 | 3/2003 | Shimamune et al. | |
| 6,544,502 B2 | 4/2003 | Heesch | |
| 6,551,492 B2 | 4/2003 | Hanaoka | |
| 6,565,736 B2 | 5/2003 | Park et al. | |
| 6,585,867 B1 | 7/2003 | Asano | |
| 6,585,868 B1 | 7/2003 | Chihara | |
| 6,620,315 B2 | 9/2003 | Martin | |
| 6,623,615 B1 | 9/2003 | Morisawa et al. | |
| 6,623,695 B2 | 9/2003 | Malchesky et al. | |
| 6,632,347 B1 | 10/2003 | Buckley et al. | |
| 6,638,364 B2 | 10/2003 | Harkins et al. | |
| 6,638,413 B1 | 10/2003 | Weinberg et al. | |
| 6,716,335 B2 | 4/2004 | Takesako et al. | |
| 6,723,226 B1 | 4/2004 | Takayasu et al. | |
| 6,743,351 B1 | 6/2004 | Arai et al. | |
| 6,752,757 B2 | 6/2004 | Muir et al. | |
| 6,815,551 B2 | 11/2004 | Albiez et al. | |
| 6,823,609 B2 | 11/2004 | Moretti | |
| 6,827,849 B2 | 12/2004 | Kurokawa et al. | |
| 6,833,206 B2 | 12/2004 | Erdle et al. | |
| 6,833,207 B2 | 12/2004 | Joos et al. | |
| 6,838,210 B2 | 1/2005 | Sawa | |
| 6,843,448 B2 | 1/2005 | Parmley | |
| 6,844,026 B2 | 1/2005 | Anthony et al. | |
| 6,852,205 B1 | 2/2005 | Toyoshima et al. | |
| 6,855,233 B2 | 2/2005 | Sawada | |
| 6,855,490 B2 | 2/2005 | Sompuram et al. | |
| 6,856,916 B2 | 2/2005 | Shyu | |
| 6,866,756 B2 | 3/2005 | Klein | |
| 6,867,048 B2 | 3/2005 | Kovacs | |
| 6,874,675 B2 | 4/2005 | Kida et al. | |
| 6,887,601 B2 | 5/2005 | Moulthrop et al. | |
| 6,921,743 B2 | 7/2005 | Scheper et al. | |
| 6,923,893 B2 | 8/2005 | Sano | |
| 2001/0012544 A1 | 8/2001 | Nagahara et al. | |
| 2001/0022273 A1 | 9/2001 | Popov et al. | |
| 2002/0023847 A1 | 2/2002 | Natsume | |
| 2002/0027070 A1 | 3/2002 | Oyokota et al. | |
| 2002/0027079 A1 | 3/2002 | Hanaoka | |
| 2002/0027084 A1 | 3/2002 | Park et al. | |
| 2002/0032141 A1 | 3/2002 | Harkins | |
| 2002/0036134 A1 | 3/2002 | Shirota et al. | |
| 2002/0074237 A1 | 6/2002 | Takesako et al. | |
| 2002/0112314 A1 | 8/2002 | Harkins | |
| 2002/0134691 A1 | 9/2002 | Satoh et al. | |

| | | |
|---|---|---|
| 2002/0135220 A1 | 9/2002 | Yamaguchi et al. |
| 2002/0160053 A1 | 10/2002 | Yahagi et al. |
| 2002/0165220 A1 | 11/2002 | Heesch |
| 2002/0165431 A1 | 11/2002 | Muir et al. |
| 2002/0168418 A1 | 11/2002 | Lorenz et al. |
| 2002/0175085 A1 | 11/2002 | Harkins et al. |
| 2002/0176885 A1 | 11/2002 | Najafi et al. |
| 2002/0179884 A1 | 12/2002 | Hoshino et al. |
| 2002/0182262 A1 | 12/2002 | Selkon |
| 2003/0015418 A1 | 1/2003 | Tseng et al. |
| 2003/0019764 A1 | 1/2003 | Baldwin et al. |
| 2003/0024828 A1 | 2/2003 | Kondo et al. |
| 2003/0045502 A1 | 3/2003 | Kataoka et al. |
| 2003/0049163 A1 | 3/2003 | Malchesky et al. |
| 2003/0056805 A1 | 3/2003 | Sumita |
| 2003/0062068 A1 | 4/2003 | Ko et al. |
| 2003/0064427 A1 | 4/2003 | Felkner et al. |
| 2003/0087427 A1 | 5/2003 | Colton et al. |
| 2003/0089618 A1 | 5/2003 | Satoh et al. |
| 2003/0098283 A1 | 5/2003 | Katayose et al. |
| 2003/0141200 A1 | 7/2003 | Harada |
| 2003/0185704 A1 | 10/2003 | Bernard et al. |
| 2003/0219361 A1 | 11/2003 | Lee et al. |
| 2003/0230826 A1 | 12/2003 | Kawaguchi et al. |
| 2004/0004007 A1 | 1/2004 | Orolin et al. |
| 2004/0011665 A1 | 1/2004 | Koizumi et al. |
| 2004/0029761 A1 | 2/2004 | Wakamatsu et al. |
| 2004/0037737 A1 | 2/2004 | Marais et al. |
| 2004/0055896 A1 | 3/2004 | Anderson et al. |
| 2004/0060815 A1 | 4/2004 | Buckley et al. |
| 2004/0079791 A1 | 4/2004 | Kida et al. |
| 2004/0081705 A1 | 4/2004 | Gotou |
| 2004/0084325 A1 | 5/2004 | Weinberg et al. |
| 2004/0084326 A1 | 5/2004 | Weinberg et al. |
| 2004/0094406 A1 | 5/2004 | Sawada |
| 2004/0131695 A1 | 7/2004 | Hinze |
| 2004/0137078 A1 | 7/2004 | Najafi et al. |
| 2004/0154993 A1 | 8/2004 | Yanagihara et al. |
| 2004/0168909 A1 | 9/2004 | Larson |
| 2004/0168933 A1 | 9/2004 | Inoue |
| 2004/0171701 A1 | 9/2004 | Shaw |
| 2004/0172985 A1 | 9/2004 | Mamiya et al. |
| 2004/0177655 A1 | 9/2004 | Kodera et al. |
| 2004/0185311 A1 | 9/2004 | Muthuswamy et al. |
| 2004/0185313 A1 | 9/2004 | Halter et al. |
| 2004/0188248 A1 | 9/2004 | Sawa |
| 2004/0208940 A1 | 10/2004 | Selkon |
| 2004/0244537 A1 | 12/2004 | Runyon |
| 2004/0250323 A1 | 12/2004 | Arai et al. |
| 2004/0254744 A1 | 12/2004 | Shyu |
| 2004/0256317 A1 | 12/2004 | Yamada et al. |
| 2004/0265394 A1 | 12/2004 | Morris et al. |
| 2005/0000117 A1 | 1/2005 | Polegato Moretti |
| 2005/0054973 A1 | 3/2005 | Constantz et al. |
| 2005/0058013 A1 | 3/2005 | Warf et al. |
| 2005/0062289 A1 | 3/2005 | Cho et al. |
| 2005/0064259 A1 | 3/2005 | Coors |
| 2005/0067300 A1 | 3/2005 | Tremblay |
| 2005/0074421 A1 | 4/2005 | Tanaka |
| 2005/0075257 A1 | 4/2005 | Scheper et al. |
| 2005/0101838 A1 | 5/2005 | Camillocci et al. |
| 2005/0109610 A1 | 5/2005 | Inamoto et al. |
| 2005/0126927 A1 | 6/2005 | Lindauer et al. |
| 2005/0126928 A1 | 6/2005 | Hung et al. |
| 2005/0129996 A1 | 6/2005 | Moulthrop et al. |
| 2005/0139465 A1 | 6/2005 | Kasuya et al. |
| 2005/0139808 A1 | 6/2005 | Alimi |
| 2005/0142157 A1 | 6/2005 | Alimi |
| 2005/0153858 A1 | 7/2005 | Anthony et al. |
| 2005/0155863 A1 | 7/2005 | Kovacs et al. |
| 2005/0161950 A1 | 7/2005 | Borden et al. |
| 2005/0178349 A1 | 8/2005 | Tse |
| 2005/0178920 A1 | 8/2005 | Wilson |
| 2005/0183949 A1 | 8/2005 | Daly et al. |
| 2005/0183964 A1 | 8/2005 | Roberts et al. |
| 2005/0189234 A1 | 9/2005 | Gibson et al. |
| 2005/0189237 A1 | 9/2005 | Sano |
| 2005/0196462 A1 | 9/2005 | Alimi |
| 2005/0198963 A1 | 9/2005 | Wai et al. |
| 2005/0209518 A1 | 9/2005 | Sage et al. |

FOREIGN PATENT DOCUMENTS

| | | |
|---|---|---|
| EP | 0 368 812 A1 | 5/1990 |
| EP | 0 601 891 A1 | 6/1994 |
| EP | 0 636 581 | 7/1994 |
| EP | 0 740 329 A | 4/1997 |
| EP | 0889007 A1 | 4/1997 |
| EP | 0826636 A1 | 3/1998 |
| EP | 0841305 A2 | 5/1998 |
| EP | 0 949 205 A1 | 10/1999 |
| EP | 1 038 993 A | 9/2000 |
| EP | 1064845 A1 | 1/2001 |
| EP | 1065265 A1 | 1/2001 |
| EP | 1 074 515 A2 | 2/2001 |
| EP | 1 103 264 A2 | 5/2001 |
| EP | 1162176 A1 | 12/2001 |
| EP | 1314699 A1 | 5/2003 |
| EP | 1386887 A1 | 2/2004 |
| GB | 2253860 A | 9/1992 |
| GB | 2352728 A | 2/2001 |
| JP | 01194993 | 8/1989 |
| JP | 01218682 | 8/1989 |
| JP | 02149395 | 6/1990 |
| JP | 05-339769 A | 12/1993 |
| JP | 06-182345 | 7/1994 |
| JP | 05228474 | 9/1994 |
| JP | 05228475 | 9/1994 |
| JP | 06254567 | 9/1994 |
| JP | 06312183 | 11/1994 |
| JP | 06335685 | 12/1994 |
| JP | 07-000966 A | 1/1995 |
| JP | 07031981 | 2/1995 |
| JP | 07-075784 A | 3/1995 |
| JP | 07-155760 | 6/1995 |
| JP | 07-214063 | 8/1995 |
| JP | 07238640 | 12/1995 |
| JP | 07323289 | 12/1995 |
| JP | 08-001160 A | 1/1996 |
| JP | 08052476 | 2/1996 |
| JP | 08-061788 | 3/1996 |
| JP | 08164192 | 6/1996 |
| JP | 08326124 | 12/1996 |
| JP | 09025236 | 1/1997 |
| JP | 09-157173 A2 | 6/1997 |
| JP | 09-290269 | 11/1997 |
| JP | 10080686 | 3/1998 |
| JP | 10-128331 A2 | 5/1998 |
| JP | 10113664 | 5/1998 |
| JP | 11-151493 A2 | 6/1999 |
| JP | 10192860 | 3/2000 |
| JP | 2001/079548 | 3/2001 |
| JP | 2000/084559 | 4/2001 |
| JP | 2001-096275 A | 4/2001 |
| JP | 2001/113276 | 6/2001 |
| JP | 2001-191076 A2 | 7/2001 |
| JP | 03-236315 B2 | 12/2001 |
| JP | 03-247134 B2 | 1/2002 |
| JP | 2002-059164 A | 2/2002 |
| JP | 03-299250 B2 | 7/2002 |
| JP | 03-338435 B2 | 10/2002 |
| JP | 03-396853 B2 | 4/2003 |
| JP | 2003/236543 | 8/2003 |
| JP | 03-458341 B2 | 10/2003 |
| JP | 2004/049946 | 2/2004 |
| JP | 2004/216349 | 8/2004 |
| JP | 2004/223306 | 8/2004 |
| JP | 2004/223309 | 8/2004 |
| JP | 2004/223310 | 8/2004 |
| JP | 2004/232413 | 8/2004 |
| JP | 2005/013520 A2 | 1/2005 |
| JP | 2005/058848 A2 | 3/2005 |
| SU | 1296156 A | 3/1987 |
| WO | WO 96/02271 | 2/1996 |
| WO | WO 9616555 | 6/1996 |
| WO | WO 97/49638 A | 12/1997 |
| WO | WO 9746489 A1 | 12/1997 |

| WO | WO 9817588 A1 | 4/1998 |
| WO | WO 98/27013 | 6/1998 |
| WO | WO 9842625 A1 | 10/1998 |
| WO | WO 9858880 A1 | 12/1998 |
| WO | WO 9900588 A2 | 1/1999 |
| WO | WO 9928238 A1 | 6/1999 |
| WO | WO 0033757 A1 | 6/2000 |
| WO | WO 0076475 A1 | 12/2000 |
| WO | WO 01/13926 | 3/2001 |
| WO | WO 01/54704 A1 | 8/2001 |
| WO | WO 02/04032 A2 | 1/2002 |
| WO | WO 03000957 A1 | 1/2003 |
| WO | WO 03024491 A2 | 3/2003 |
| WO | WO 03/042111 A2 | 5/2003 |
| WO | WO 03/048421 A1 | 6/2003 |
| WO | WO 03076688 A2 | 9/2003 |
| WO | WO 03103522 A1 | 12/2003 |
| WO | WO 2004076721 A1 | 9/2004 |
| WO | WO 2004078654 A2 | 9/2004 |
| WO | WO 2004079051 A1 | 9/2004 |
| WO | WO 2004081222 A2 | 9/2004 |
| WO | WO 2004082690 A1 | 9/2004 |
| WO | WO 2004092571 A1 | 10/2004 |
| WO | WO 2005003848 A1 | 1/2005 |
| WO | WO 2005011417 A2 | 2/2005 |
| WO | WO 2005020896 A2 | 3/2005 |
| WO | WO 2005030651 A1 | 4/2005 |
| WO | WO 2005/065383 A2 | 7/2005 |
| WO | WO 2005061394 A1 | 7/2005 |
| WO | WO 2005075581 A1 | 8/2005 |
| WO | WO 2005080639 12 | 9/2005 |
| WO | WO 2005082176 A1 | 9/2005 |

OTHER PUBLICATIONS

European Search Report for EP 1 103 264, 2003.
International Search Report for PCT/US02/38861, 2003.
European Search Report for EP 1 293 481, 2003.
Supplementary European Search Report for EP 02 79 0029, 2005.
Ayliffe, "Working Party Report: Decontamination of minimally invasive surgical endoscopes and accessories," *Journal of Hospital Infection*, 45, 263-277 (2000).
Badia, et al., "Saline Wound Irrigation Reduces the Postoperative Infection Rate in Guinea Pigs." *Journal of Surgical Research*, 63, 457-459 (1996).
Beckman, et al., "The free radical theory of aging matures," *Physiol. Rev.* 78, 547-581 (1998).
Chisholm, "Wound Evaluation and Cleansing." *Soft Tissue Emergencies*, 10(4), 665-672 (1992).
Dire, et al., "A Comparison of Wound Irrigation Solutions Used in the Emergency Department," *Ann Emerg Med.*, 19(6), 704-8 (1998).
Dyson, et al., "Comparison of the Effects of Moist and Dry Conditions on Dermal Repair," *Journal for Investigative Dermatology*, 91(5), 434-439 (1988).
Erwin-Toth, et al., "Wound Care Selecting the Right Dressing," *Am J Nurs.*, 95(2), 46-51 (1995).
Field, et al., "Overview of Wound Healing in a Moist Environment," *Am J Surg.*, 167(1A), 2S-6S (1994).
Higgins, et al., "Wound dressings and Topical Agents." *The Diabetic Foot*, 12(1), 31-40, (1995).
Hinman, et al., "Effect of Air Exposure and Occlusion on Experimental Human Skin Wounds," *Nature*, 200, 377-379 (1963).
Hollander, et al., "Laceration Management," *Annals of Emergency Medicine*, 34(3), 356-367 (1999).
Horita, et al., "Healing of Fournier's gangrene of the scrotum in a haemodialysis patient after conservative therapy alone," *Nephrology Dialysis Transplantation*, 15 (3), 419-421 (2000).
Jeter, et al., "Wound Dressings of the Nineties: Indications and Contraindications," *Wound Healing*, 8(4), 799-816 (1991).
Koseki, et al., "Effect of mild heat pre-treatment with alkaline electrolyzed water on the efficacy of acidic electrolyzed water against *Escherichia coli* O157:H7 and *Salmonella* on lettuce," *Food Microbiology*, 21(5), 559-566 (2004).
Loshon, et al., "Analysis of the killing of spores of *Bacillus subtilis* by a new disinfectant, Sterilox," *Journal of Applied Microbiology*, 91, 1051-1058 (2001).
Madden, et al., "Application of Principles of Fluid Dynamics to Surgical Wound Irrigation," source unknown, (1971).
Marnett, "Oxyradicals and DNA damage," *Carcinogenesis*, 21, 361-370 (2000).
Martinez, "Sterilant for Human Wounds is Changing Patients' Lives" *Infection Control Today*, (2004).
Middleton, et al., "Comparison of a solution of super-oxidized water (Sterilox) with glutaraldehyde for the disinfection of bronchoscopes, contaminated in vitro with *Mycobacterium tuberculosis* and *Mycobacterium avium-intracellulare* in sputum," *Journal of Hospital Infection*, 45, 278-282 (2000).
Miranda-Altamirano et al., "Treatment of $2^{nd}$ and $3^{rd}$ Degree Burns in 48 Pediatric Patients Without Routine Antibiotics Routine Using New Super-oxidized Water Technology" Abstract for Meeting of the Texas Surgical Society, Apr. 1-3, 2005.
Moscati, et al., "Comparison of Normal Saline with Tap Water for Wound Irrigation," *American Journal of Emergency Medicine*, 16(4), 379-385 (1998).
Nakagawara, et al., "Spectroscopic characterization and the pH dependence of bactericidal activity of the aqueous chlorine solution," *Analytical Sciences*, 14(4), 691-698 (1998).
Ohno, et al., "Mediastinal Irrigation with Superoxidized Water After Open-Heart Surgery: The Safety and Pitfalls of Cardiovascular Surgical Application," *Surgery Today*, 30, 1055-1056 (2000).
Piaggesi, et al., "Sodium carboxyl-methyl-cellulose dressings in the management of deep ulcerations of diabetic foot," *Diabet Med.*, 18(4), 320-4 (2001).
Rodeheaver, et al., "Identification of the Wound Infection-Potentiating Factors in Soil," *American Journal of Surgery*, 128(1), 8-14, (1974).
Ruddy, et al., "Decontamination in Practice: Endoscopic decontamination: an audit and practical review," *Journal of Hospital Infection*, 50, 261-268 (2002).
Rutala ,et al., "New Disinfection and Sterilization Methods," *Centers for Disease Control and Prevention (CDC): Emerging Infectious Diseases*, 7 (2), 348-353 (2001).
Sekiya, et al., "Treatment of Infectious Skin Defects or Ulcers with Electrolyzed Strong Acid Aqueous Solution," *Artificial Organs*, 21 (1), 32-38 (1997).
Selkon,et al., "Evaluation of the antimicrobial activity of a new super-oxidized water, Sterilox®, for the disinfection of endoscopes," *Journal of Hospital Infection*, 41, 59-70 (1999).
Shen, et al., "Interactions of selenium compounds with other antioxidants in DNA damage and apoptosis in Human normal keratinocytes," *Cancer Epidemiol Biomarkders Prev.*, 10, 385-390 (2001).
Shetty, et al., "Evaluation of microbicidal activity of a new disinfectant: Sterilox® 2500 against *Clostridium difficile* spores, *Helicobacter pylori*, cancomycin resistant *Enterococcus* species, *Candida albicans* and several Mycobacterium species," *Journal of Hospital Infection*, 41, 101-105 (1999).
Shimmura, et al., "Acidic Electrolyzed Water in the Disinfection of the Ocular Surface," *Experimental Eye Research*, 70(1), 1-6 (2000).
Singer, et al., "Evaluation and Management of Traumatic Lacerations," *New England Journal of Medicine*, 1142-1148 (1997).
Solovyeva, et al., "Cleaning effectiveness of root canal irrigation with electrochemically activated anolyte and catholyte solutions: a pilot study," *International Endodontic Journal*, 33, 494-504 (2000).
Stevenson, et al., "Cleansing the Traumatic Wound by High Pressure Syringe Irrigation." *JACEP*, 5(1), 17-21 (1976).
Tanaka, et al., "Antimicrobial activity of superoxidized water" *Journal of Hospital Infection*, 34, 43-49 (1996).
Upright, et al., "Evaluation of Mesalt dressings and continuous wet saline dressings in ulcerating metastatic skin lesions," *Cancer Nursing*, 17(2), 149-155 (1994).
Venkitanarayanan, et al., "Efficacy of Electrolyzed Oxidizing Water for Inactivating *Escherichia coli* O157:H7, *Salmonella enteritidis*, and *Listeria monocytogenes*," *Applied and Environmental Microbiology*, 65 (9), 4276-4279 (1999).
Veves, et al., "A randomized, controlled trial of Promogran (a collagen/oxidized regenerated cellulose dressing) vs standard treatment in the management of diabetic foot ulcers," *Arch Surg.*, 137(7), 822-7 (2002).

Winter, "Formation of the Scab and the Rate of Epithelization of Superficial Wounds in the Skin of the Young Domestic Pig," *Nature*, 193, 293-294 (1962).

Xakellis, et al., "Hydrocolloid versus saline-gauze dressings in treating pressure ulcers: a cost-effectiveness analysis," *Arch Phys Med Rehabil.*, 73(5), 463-9 (1992).

Yahagi, et al., "Effect of Electrolyzed Water on Wound Healing," *Artificial Organs*, 24 (12), 984-987 (2000).

Zinkevich, et al., "The effect of super-oxidized water on *Escherichia coli*," *Journal of Hospital Infection*, 46, 153-156 (2000).

Communication from the International Searching Authority dated Oct. 4, 2005 for PCT/US2004/043961 (including partial international search report).

Arrigo, et al., "Cytotoxic effects induced by oxidative stress in culture mammalian cells and protection provided by Hsp27 expression," (2005) (source unknown).

Bari, et al., "Chemical and irradiation treatments for killing *Escherichia coli* O157:H7 on alfalfa, radish, and mung bean seeds," *J Food Prot.*, 66(5), 767-74 (2003).

Bari, et al., "Effectiveness of electrolyzed acidic water in killing *Escherichia coli* O157:H7, *Salmonella enteritidis*, and *Listeria monocytogenes* on the surfaces of tomatoes," *J Food Prot.*, 66(4), 542-8 (2003).

Boulton, *The Diabetic Foot*. "Diabetes: Clinical Management." Chapter 26, 293-306, (1990).

Carlson, "Redox media as a factor in destroying germs," *Schriftenreihe des Vereins fuer Wasser-, Boden- und Lufthygiene*, 31, 21-39 (1970).

Carton, et al., "Hypotonicity induces membrane protrusions and actin remodeling via activation of small GTPases Rac and Cdc42 in Rat-1 fibroblast," *Am. J. Physiol. Cell. Physiol.*, 285, C935-C944 (2003).

Chernomorskii, "Diagram of the electrochemical stability of water", *Zhurnal Fizicheskoi Khimii*, 51(4), 924-925 (1977).

De Grey, "Reactive oxygen species production in the mitochondrial matrix: implications for the mechanism of mitochondrial mutation accumulation," *Rejuvenation Res.*, 8(1), 13-17 (2005).

Dressler, "Standards and Histogram Interpretation in DNA Flow Cytometry," *Methods in Cell Biology*, 41, 241-262 (1994).

Fabrizio, et al., "Comparison of electrolyzed oxidizing water with various antimicrobial interventions to reduce *Salmonella* species on poultry," *Poult. Sci.*, 81(10), 1598-605 (2002).

Flint, et al., "Virus cultivation, detection and genetics," Chapter 2, *Principles of Virology, Molecular Biology, Pathogenesis and Control*, ASM Press 2000; 32.

Fraise, "Choosing disinfectants," *J Hosp infect*, 43, 255-264 (1999).

Fraga, et al., "Ascorbic acid protects against endogenous oxidative DNA damage in human sperm," *Proc. Natl. Acad. Sci USA*, 88, 11003-11006 (1991).

Frippiat, et al., "Subcytotoxic $H_2O_2$ stress triggers a release of transforming growth factor-beta, which induces biomarkers of cellular senescence of human diploie fibroblast," *J. Biol. Chem.* 276, 2531-2537 (2001).

Fromin, et al:, "Participation of water [hydroxyl ions] in oxidation-reduction processes," *Sostoyanie Rol Vody Biol. Ob'ektakh, Simp., Tiflis*, 120-131 (1967).

Gao, et al., "Observation on the effect of disinfection to HBs Ag by electrolyzed oxidizing water," *Zhonghua Liu Xing Bing Xue Za Zhi*, 22, 40-42 (2001).

Goberdham, et al., "A biomarker that identifies senescent human cell in culture and in aging skin in vivo," *Proc. Natl. Acad. Sci. USA*, 92, 9663-9667 (1995).

Guitierrez, et al., "Produccion de agents biologicos par alas terapias genicas y celulares en humanos," *Diagnostico molecular en medicine*, 265-291 (2003).

Harada, "Behavior of hydrogen peroxide in electrolyzed anode water," *Biosci. Biotechnol Biochem.*, 66(9), 1783-91 (2002).

Hatto, et al., "The physiological property and function of the electrolyzed-ionized calcium Aquamax on water molecular clusters fractionization," *Artif. Organs*, 21(1), 43-9 (1997).

Hayashi, et al., "Successful treatment of mediastinitis after cardiovascular surgery using electrolyzed strong acid water aqueous solution," *Artif Organs*, 21, 39-42 (1997).

Horiba, et al., "Bactericidal effect of electrolyzed neutral water on bacteria isolated from infected root canals," *Oral Surg Oral Med Oral Pathol Oral Radiol Endod*, 87, 83-87 (1999).

Inoue, et al., "Trial of electrolyzed strong acid aqueous solution lavage in the treatment of peritonitis and intraperitoneal abscess," *Artif Organs*, 21, 28-31 (1997).

Ivanova, et al., "Mechanism of the extracellular antioxidant defend," *Experimental pathology and parasitology*, 4, 49-59 (2000).

Iwasawa, et al., "Bactericidal effect of acidic electrolyzed water—comparison of chemical acidic sodium hydrochloride (NaOCl) solution," *Kansenshogaku Zasshi*,; 70(9), 915-22 (1996).

Iwasawa, et al., "The influence of pH on bactericidal effects of strong acidic electrolyzed water," *Bokin Bobai*, 30(10), 635-643, (2002).

Kaufman, "Preventing Diabetic Foot Ulcers," *Derm. Nurs.*, 6(5), 313-320 (1994).

Kiura, et al., "Bactericidal activity of electrolyzed acid water from solution containing sodium chloride at low concentration, in comparison with that at high concentration," *J Microbiol Methods*, 49(3), 285-93 (2002).

Kim, et al., "Efficacy of electrolyzed oxidizing water in inactivating *Salmonella* on alfalfa seeds and sprouts," *J Food Prot.*, 66(2), 208-14 (2003).

Kim, et al., "Roles of oxidation-reduction potential in electrolyzed oxidizing and chemically modified water for the inactivation of food-related pathogens," *J Food Prot*, 63, 19-24 (2000).

Kimbrough, et al., "Electrochemical removal of bromide and reduction of THM formation potential in drinking water," *Water Res.*, 36(19), 4902-6 (2002).

Kitaoka, "On the electrolytic separation factor of tritium," *Radioisotopes*, 30(5), 247-52 (1981).

Koseki, et al., "Effect of nitrogen gas packaging on the quality and microbial growth of fresh-cut vegetables under low temperatures," *J Food Prot.*, 65(2), 326-32 (2002).

Koseki, et al., "Decontaminative effect of frozen acidic electrolyzed water on lettuce," *J Food Prot.*, 65(2), 411-4 (2002).

Koseki, et al., "Decontamination of lettuce using acidic electrolyzed water," *J Food Prot.*, 64(5), 652-8 (2001).

Koseki, et al., "Prediction of microbial growth in fresh-cut vegetables treated with acidic electrolyzed water during storage under various temperature conditions," *J Food Prot.*, 64(12), 1935-42 (2001).

Laing, "Diabetic Foot Ulcers," *Am J Surg*, 167, 31S-26S (1994).

Len, et al., "Ultraviolet spectrophotometric characterization and bactericidal properties of electrolyzed oxidizing water as influenced by amperage and pH," *J Food Prot*, 63, 1534-1537 (2000).

Len, et al., "Effects of storage conditions and pH on chlorine loss in electrolyzed oxidizing (EO) water," *J Agric Food Chem*, 50, 209-212 (2002).

Li, et al., "Preliminary study of microbiocide effect and its mechanism of electrolyzed oxidizing water," *Zhonghua Liu Xing Bing Xue Za Zhi*, 7, 95-98 (1996).

Mangram, et al., "Guideline for prevention of surgical site infection," *Infection Control and Hospital Epidemiology*, 1999, 20(4), 247-278 (1999).

Michida, et al., "Biomimetic oxidation of diphenyl sulfide with electrochemical P-450 model system in CH2C12 treated with alkaline solution," *Yakugaku Zasshi*, 119(10), 780-5 (1999).

Minimal Access Therapy Decontamination Working Group, "Decontamination of minimally invasive surgical endoscopes and accessories," *J Hosp. Infect*, 45, 263-277 (2000).

Miyamoto, et al., "Effectiveness of acidic oxidative potential water in preventing bacterial infection in islet transplantation," *Cell Transplant*, 8, 405-411 (1999).

Model, et al., "Effectiveness of electrolyzed oxidized water irrigation in a burn-wound infection," *J Trauma Injury, Infection, and Critical Care*, 49, 511-514 (2000).

Morita, et al., "Disinfection potential of electrolyzed solution containing sodium chloride at low concentrations," *J Virol Methods*, 85, 163-174 (2000).

Moyer, et al., "Modulation of human fibroblast Gap junction intercellular communication by Hyaluronan," *J. Cell. Biol.* 196, 165-170 (2003).

Naderi, et al., "Oxidative stress-induced apoptosis in dividing fibroblast involves activation of p38 MAP kinase and over expression of Bax: Resistance of quiescent cells to oxidative stress," *Apoptosis*, 8, 91-100 (2003).

Nagamatsu, et al., "Application of electrolyzed acid water to sterilization of denture base part 1. Examination of sterilization effects on resin plate," *Dent. Mater J*, 20(2), 148-55, (2001).

Nagamatsu, et al., "Durability of bactericidal activity in electrolyzed neutral water by storage," *Dent Mater J*, 21, 93-104 (2002).

Nakae, et al., "Effectiveness of electrolyzed oxidized water irrigation in a burn-wound infection model," *J Trauma*, Sep.; 49(3): 511-4 (2000).

Nakagawa, et al., "Effect of rinsing hydrocolloid impressions using acidic electrolyzed water on surface roughness and surface hardness of stone models," *J Oral Sci.*, 44(3-4), 141-6 (2002).

Nelson, "Newer technologies for endoscope disinfection: electrolyzed acid water and disposable-component endoscope systems," *Gasatrointest Endosc Clin N Am*, 10, 319-328 (2000).

Ogino, et al., "Treatment for abdominal aortic graft infection: irrigation with electrolyzed strong aqueous acid, in-situ grafting, and omentoplasty," *Thorac Cardiovasc Surg*, 48(1), 43-44 (2000).

Okubo, et al., "Cytotoxicity and microbicidal activity of electrolyzed strong acid water and acidic hypochlorite solution under isotonic conditions," *Kansenshogaku Zasshi*, 73(10), 1025-31 (1999).

O'Neill, "Physiological significance of volume-regulatory transporters," *Am. J. Physiol.* 276, C995-C1001 (1999).

Oomori, et al., "The efficiency of disinfection of acidic electrolyzed water in the presence of organic materials," *Anal Sci*, 16, 265-369 (2000).

Ottender, et al., "Correlation of DNA adduct levels with tumor incidence: carcinogenic potency of DNA adducts," *Mutat. Res.*, 424, 237-247 (1999).

Park, et al., "Antimicrobial effect of electrolyzed water for inactivating *Campylobacter jejuni* during poultry washing," *International Journal of Food Microbiology*, 72(1-2), 77-83 (2002).

Park, "Effectiveness of electrolyzed water as a sanitizer for treating different surfaces," *J Food Prot.*, 65(8), 1276-80 (2002).

Park, et al., "Effects of chlorine and pH on efficacy of electrolyzed water for inactivating *Escherichia coli* O157:H7 and *Listeria monocytogenes*," *International Journal of Food Microbiology*, 91(1), 13-18 (2004).

Powis, et al., "Redox signaling and the control of cell growth and death," *Pharmacol Ther.*, 68, 149-173 (1995).

Russell, "The effect of electrolyzed oxidative water applied using electrostatic spraying on pathogenic and indicator bacteria on the surface of eggs," *Poult. Sci.*, 82(1), 158-62 (2003).

Sakai, "Development of ionic electrolyzed water and its utilities. The preparation of ionic electrolyzed water and its application to disinfection," *Kurin Tekunoroji* (1996), 6(3), 53-57 (1996).

Sakashita, et al., "Antimicrobial effects and efficacy on habitually hand-washing of strong acidic electrolyzed water—a comparative study of alcoholic antiseptics and soap and tap water", *Kansenshogaku Zasshi* 76, 373-377 (2002).

Sanders, "Diabetes Mellitus: Prevention of Amputation," *J Am Pod Med Assoc*, 84(7), 322-328 (1994).

Sawada, "Complete electrolysis using a microflow cell with an oil/water interface." *Anal Chem.*, 74(5), 1177-81 (2002).

Severino, et al., "Is β-galactosidase staining a marker of senescence in vitro and in vivo?" *Exp. Cell. Res.*, 257, 162-171 (2000).

Sharma, et al., "Treatment of *Escherichia coli* O157:H7 inoculated alfalfa seeds and sprouts with electrolyzed oxidizing water," *International Journal of Food Microbiology*, 86(3), 231-237 (2003).

Shirahata, et al., "Electrolyzed-reduced water scavenges active oxygen species and protects DNA from oxidative damage," *Biochem. Biophys. Res. Commun.*, 234(1), 269-74 (1997).

Smirnov, et al., "Electron exchangers and electron- and ion-exchangers and their use in a water treatment system," *Khim. Aktiv. Polim. Ikh Primen*, 259-262 (1969).

Soto, et al., "Bacterial sulfate production by biodesulfurization of aromatic hydrocarbons, determined by ion chromatography," *J Chromatogr A*, 824(1), 45-52 (1998).

Stein, "SV-40-transformed human fibroblasts: evidence for cellular aging in pre-crises cells," *J Cell, Physiol*, 125, 36-44 (1985).

Sumita, "Characteristics and use of acidified water from redox water generator," *Shokuhin Kogyo*, 40(10), 29-36 (1997).

Suzuki, "Novel products generated from 2'-deoxyguanosine by hypochlorous acid or a myeloperoxidase —$H_2O_2$-CI-system: identification of diimino-imidazole and amino-imidazolone nucleosides," *Nucleic Acids Res.*, 30, 2555-2564 (2002).

Tanaka, et al., "The use of electrolyzed solutions for the cleaning and disinfecting of dialyzers" *Artif. Organs*, 24(12), 921-8 (2000).

Tanaka, et al., "Molecular basis of antiapoptotic effect of immunophilin ligands on hydrogen peroxide-induced apoptosis in human glioma cells," *Neurochem Res.*, 29(8), 1529-36 (2004).

Takeshita, et al., "Influence of free residual chlorine concentration and pH on bactericidal effects of electrolyzed water," *Bokin Bobai*, 29(2), 69-72 (2001).

Takeyoshi, et al., "Primary eye irritation and 5-day cumulative skin irriation studies of super oxidized water in rabbits," *Oyo Yakuri*, 48(3), 173-177 (1994).

Tateno, et al., "MT-4 plaque formation can distinguish cytopathic substypes of the human immunodeficiency virus (HIV)," *Virology*, 167, 299-301 (1988).

Valko, et al., "Role of oxygen radicals in DNA damage and cancer incidence," *Mol Cell Biochem*, 266, 37-56 (2004).

Van Britsom, et al., "A rapid method for the detection of uranium in surface water," *Sci. Total Environ.*, 173-174, 83-9 (1995).

Yang, et al., "The effect of pH on inactivation of pathogenic bacteria on fresh-cut lettuce by dipping treatment with electrolyzed water," *Journal of Food Science*, 68(3), 1013-1017 (2003).

Yoshimoto, et al., "Virucidal effect of super oxidized water" *Kagaku Ryoho no Ryoiki*, 12(7), 1337-1342 (1996).

Young, et al., "Mechanisms of killing of *Bacillus subtilis* spores by hypochlorite and chlorine dioxide," *J Appl Microbiol*, 95, 54-67 (2003).

Zhang, et al., "Antioxidant superoxide dismutase attenuates increased endothelial permeability induced by platelet activating factor," *Soc Gynecol Investig.* 10, 5-10 (2003).

International Search Report for PCT/US2006/011251 (Sep. 14, 2006).

Written Opinion for PCT/US2006/011251 (Sep. 14, 2006).

International Search Report for PCT/US2006/011252 (Nov. 10, 2006).

Written Opinion for PCT/US2006/011252 (Nov. 10, 2006).

* cited by examiner

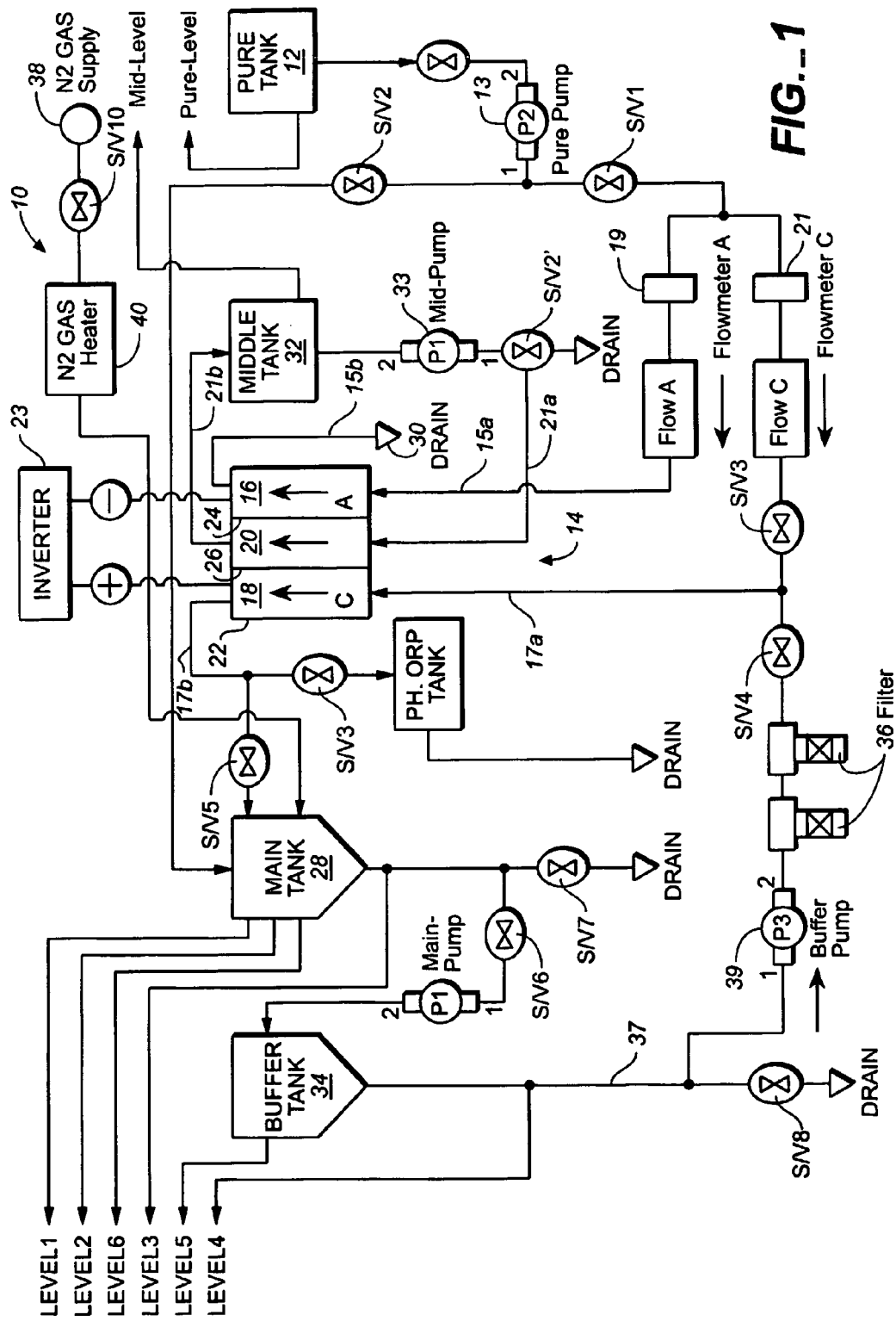
FIG._1

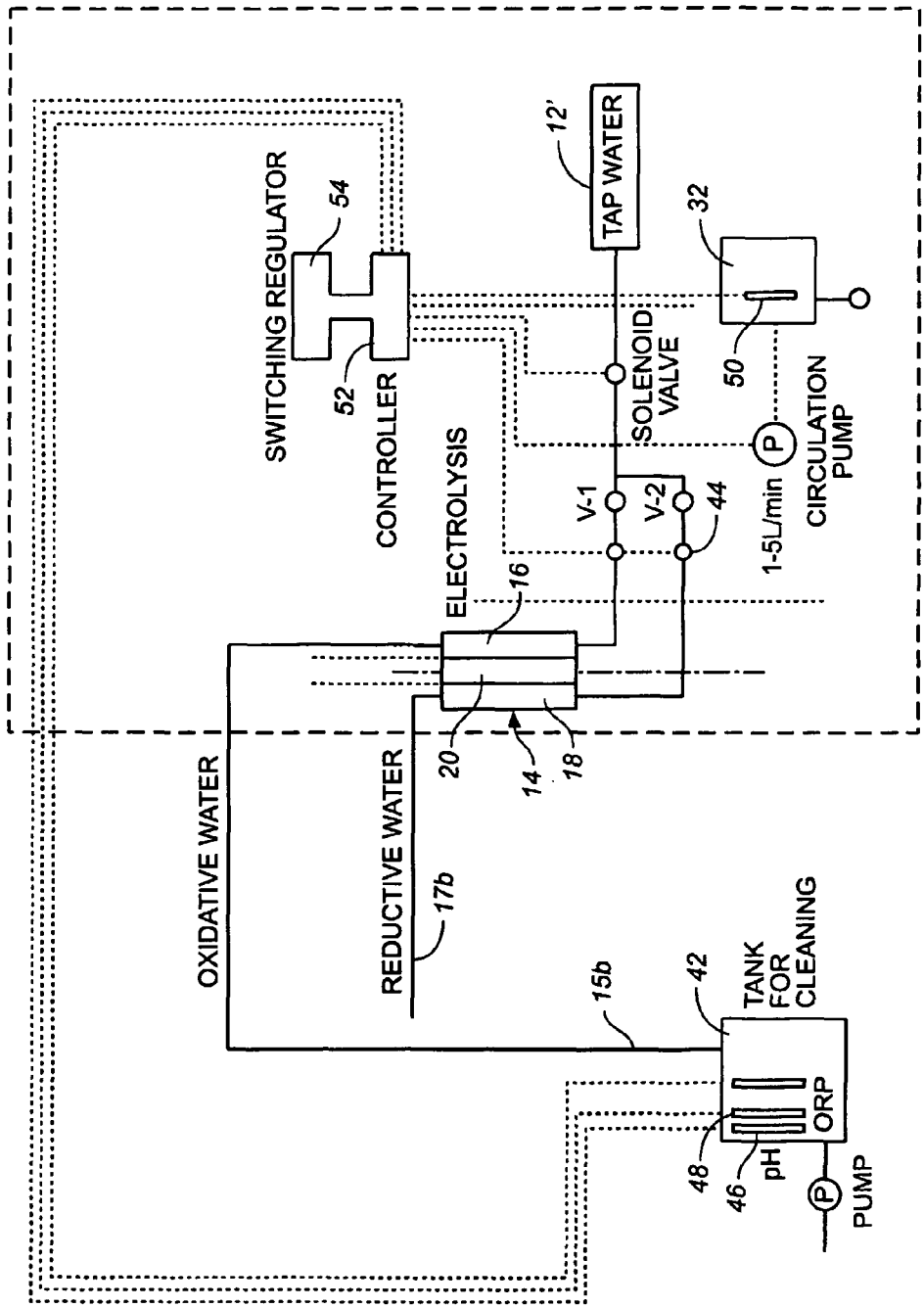
FIG._2

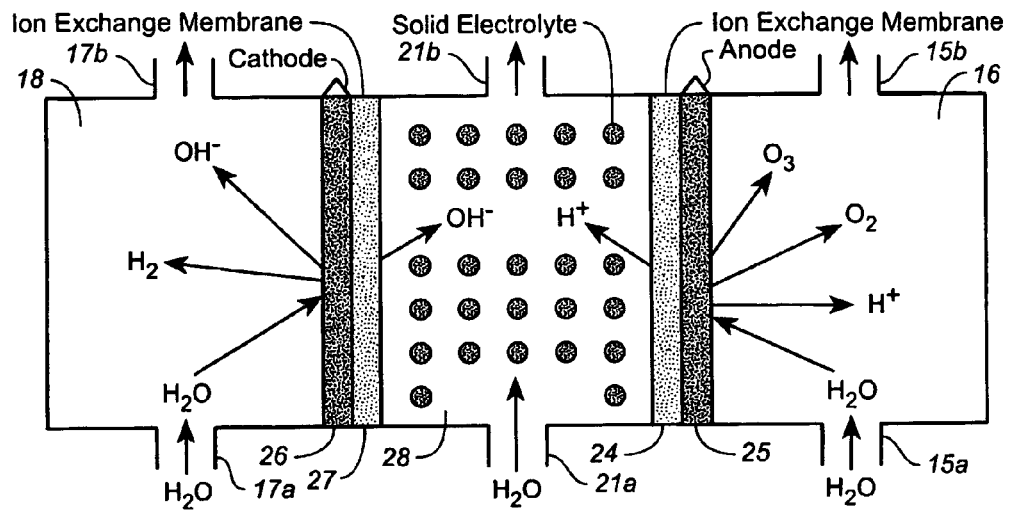
FIG._3
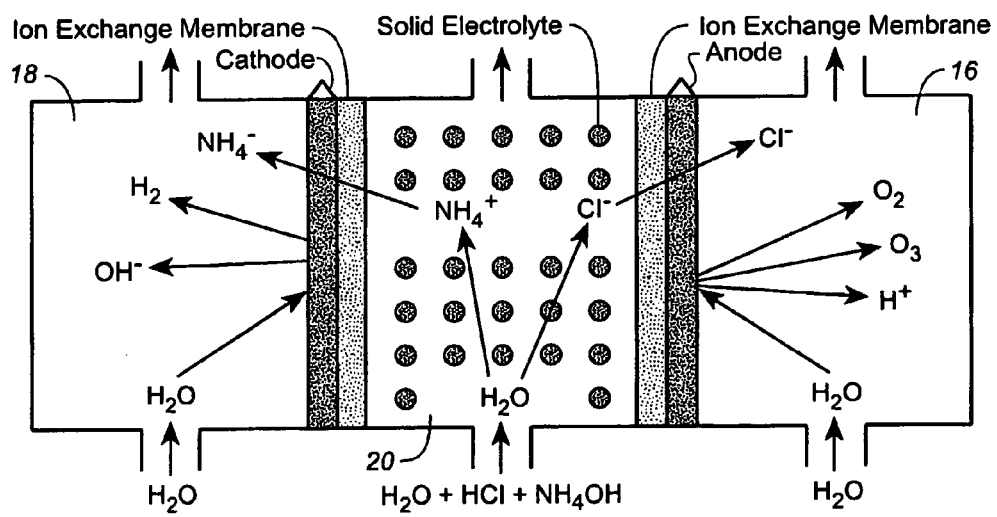
FIG._4

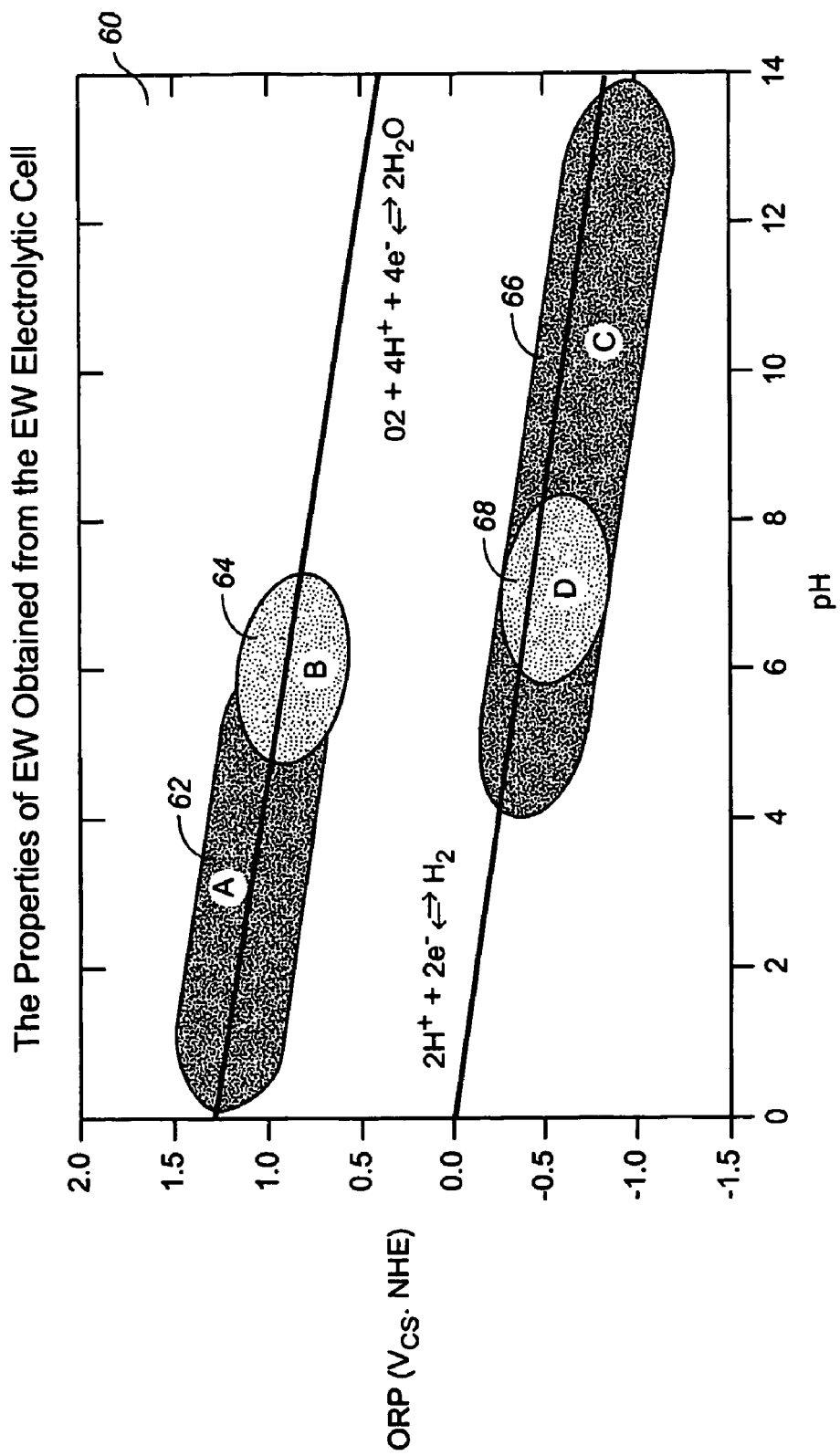
FIG._5

EW Life Time

| Cell Type | pH of EW | | Cl Concentration of EW(ppm) | ORP (mV/Ag/AgCl) | Life Time | |
|---|---|---|---|---|---|---|
| | Anode Water | Cathode Water | | | Closed | Open |
| TYPE 1 | 2.3 - 3.5 | 11.5 - 12.2 | 10 - 100 | 1,050 - 1,180 | 3 month | 10 Day |
| TYPE 2 | 3.0 - 4.0 | 7.5 - 9.5 | 0.4 - 20 | 1,000 - 1,140 | 24 Hrs | 3 Hrs |
| TYPE 3 | 5.6 - 6.0 | 7.5 - 9.5 | 0 | 900 - 1,050 | 1 Hr | 20 Mins |

\* EW Life Time depends on Cell Type, Electrolyte and DI water
\* Used PET & PP bottle

FIG._6

METHOD AND APPARATUS FOR PRODUCING NEGATIVE AND POSITIVE OXIDATIVE REDUCTIVE POTENTIAL (ORP) WATER

BACKGROUND OF THE INVENTION

1. Technical Field

The present invention relates generally to acidic and alkaline/oxidative and reductive potential water (ORP water) and to methods of electrolyzing saline solutions. More particularly, the present invention relates to a method and apparatus for producing negative and positive ORP water, and the water so produced, for use in sterilization, decontamination, disinfection, skin cleansing, and wound healing catalysis.

2. Background Art

The production of super-oxidized water is an electrochemical, or oxidation-reduction process. This is commonly referred to as an electrolytic or redox reaction in which electrical energy is used to produce chemical change in an aqueous solution. Electrical energy is introduced into and transported through water by the conduction of electrical charge from one point to another in the form of an electrical current. In order for the electrical current arise and subsist there must be charge carriers in the water, and there must be a force that makes the carriers move. The charge carriers can be electrons, as in the case of metal and semiconductors, or they can be positive and negative ions in the case of solutions.

It is difficult to force electrical energy, or current, through pure water since it is not a charge carrier and is not ionic in and of itself. Absolutely pure water, while theoretically simple is, as a practical matter, virtually impossible to obtain. Hence, water in the form we commonly encounter it can and does conduct electrical energy, or current, due to the presence of dissolved ions. The greater the concentration of dissolved ions, the greater the ability to conduct current and the ability to produce a chemical change in the solution.

Since water is never pure it can contain numerous dissolved substances. It invariably contains trace amounts of $H_3O^+$ and $OH^-$ from the dissociation of water. It can also contain dissolved gases, such as $CO_2$ and $N_2$ that can also be reactants. Water also contains various anions and cations. As is well known, the $H_2O$ molecule is polar; that is, it has an unequal charge distribution. This is due to the molecular structure and the unequal attraction for electrons exerted by the oxygen and hydrogen atoms comprising the molecule. This polarity significantly enhances water's ability to dissolve numerous substances, including ionic compounds such as sodium chloride or salt.

Molecules of water can either be oxidized to $O_2$ by the removal of electrons or reduced to $H_2$ by the addition of electrons. Therefore water must always be considered a possible reactant. Typical reactions occur at either the cathode or the anode.

At the cathode reduction must occur. Many different reactions are possible however the following two reactions are the most likely:

$$2H_2O + 2e^- \rightarrow H_2(gas) + 2OH^-$$

$$2H_3O + 2e^- \rightarrow H_2(gas) + 2H_2O$$

There are several other possible reactions at the cathode, none of which are easy to predict. It is necessary to consider which reactant is most easily reduced and which is reduced most rapidly. The strongest oxidizing agent is not necessarily the fastest. Complications may arise when electric current is very large and the concentration of the reactants is very small.

In the presence of NaCl other reactions are to be considered, such as the evolution of chlorine and hydrogen gas and the production of $OH^-$. The $OH^-$ or hydroxyl ion can cause significant increases in pH. In the electrolysis of NaCl, solutions show that $OH^-$ accumulates around the cathode. Cations move toward the cathode and anions toward the anode.

At the anode oxidation must occur. The most common reaction in the presence of aqueous NaCl gives rise to chlorine gas.

$$2Cl^- - 2e^- \rightarrow Cl_2(gas)$$

The overall reaction during the electrolysis of aqueous NaCl solutions shows the concentration of chlorine decreasing and the concentration of $OH^-$ increasing. This condition in turn leads to other reactions and subsequent products. Chlorine gas is partly dissolved in the solution, and reacts to produce hypochlorous acid according to the following equation.

$$Cl_2 + H_2O \rightarrow HClO \text{ and } HCl$$

The resulting hydrochloric acid, HCl, can cause a significant drop in pH. There is also the possibility that the formation of HCl gives rise to other reactions simultaneously, but to an unknown degree. The production of atomic oxygen is possible; however due to the instability it is not present for long or in high concentration. This reactivity can give rise to other products such as oxygen gas, hydrogen peroxide, and ozone.

Combining the foregoing reactions and the resulting products and varying the process inputs and conditions, such as the amount and type of current, type and concentration of dissolved ions, and water purity, will give rise to water of varying characteristics.

All of the above-described reactions, when allowed to occur under controlled and optimal conditions, can result in the production of water that contains oxidized species resulting in something termed "super-oxidized water." Super-oxidized water may have varying characteristics, including either high or low pH, varying chlorine and chlorine compound content, and varying degrees of oxygen and oxygen-containing compounds.

The most easily quantifiable characteristic of super-oxidized water is its pH. Depending upon the configuration of the electrolytic cell, high pH water can be produced in the cathode chamber and low pH water can be produced in the anode chamber. These can be referred to as anode or cathode water. Low pH (acidic) anode water also has chlorine present in various forms; i.e., chlorine gas, chloride ion, hydrochloric acid, or hypochlorous acid. Oxygen in various forms can also be present. The alkaline cathode water may have hydrogen gas present along with sodium ion. The process water streams from these two electrolytic cells or chambers can be separated and analyzed.

Work performed in Japan has shown that each of the two types of water produced have unique properties. One of these properties is referred to as oxidation-reduction potential (ORP). This potential can be quantified using the standard technique of measuring the electrical potential in millivolts relative to a standard reference silver/silver chloride electrode. ORPs of approximately 1000 mV have been measured. Optical absorption spectra and electron spin resonance have showed the presence of hypochlorous acid.

It has long been known in the general art of sterilization that heat, filtration, radiation, and chemicals may be employed to remove unwanted microorganisms. However, only recently have developments in the art of electrolysis provided an alternative method of microbial disinfection and sterilization. Relatively recently, apparatus have been devised to optimize the conditions that favor the production of certain end products, including both cathode and anode water of varying ORP and residual chlorine content. Super-oxidized water has a limited shelf life and decreasing activity over time. Data shows that ORP water may be effective when used in sterilization, decontamination, disinfection, skin cleansing, and wound healing catalysis.

Relevant prior art includes U.S. Pat. No. 5,932,171 to Malchesky, issued Aug. 3, 1999, which discloses a sterilization apparatus utilizing catholyte and anolyte solutions produced by electrolysis of water. The apparatus includes a tray with an article receiving area, such that an article to be microbially decontaminated is positioned in the receiving area and a microbe blocking lid is closed over the article. A water electrolysis apparatus receives water, splits the water into two separate streams that pass respectively through an anode chamber and a cathode chamber, and exposes the streams to an electric field that results in the production of a catholyte solution for cleaning and an anolyte solution for sterilization. The anolyte and catholyte are selectively circulated through the article receiving area by a pump to clean and microbially decontaminate the external surfaces and internal passages of an article located therein. The anolyte or deactivated anolyte provides a sterile rinse solution. A reagent dispensing well receives an ampule or the like. The ampule contains internal compartments which are selectively accessed or opened to dispense detergent concentrate and/or sterilant concentrate reagents into the circulating anolyte and catholyte solutions. A water treatment apparatus dispenses either a salt or a cleaning agent into the water received from the source to vary the electrolysis reaction or to form a cleaning solution to clean and flush the electrolysis apparatus, respectively.

U.S. Pat. No. 6,171,551 to Malchesky, et al., issued Jan. 9, 2001 teaches a method of and apparatus for electrolytically synthesizing peracetic acid and other oxidants. The electrolysis unit has an ion selective barrier for separating an anodic chamber from a cathodic chamber. An electrolyte within the unit includes a precursor, such as potassium acetate, or acetic acid. A positive potential is applied to an anode within the anodic chamber, resulting in the generation of a variety of shorter and longer lived oxidizing species, such as peracetic acid, hydrogen peroxide, and ozone. In one preferred embodiment, a solution containing the oxidizing species is transported to a site where articles, such as medical instruments, are to be decontaminated. The oxidizing species are generated as needed, avoiding the need to store hazardous decontaminants.

U.S. Pat. No. 5,507,932 to Robinson, issued Apr. 16, 1996, teaches an apparatus for electrolyzing fluids. The device ostensibly produces electrolyzed fluids that are Particularly suited for treating physiological materials such as whole blood, plasma, or cell isolates in order to reduce the effect of harmful microorganisms. A container holds the fluid and a power supply provides a source of electrical current to an anode and a cathode positioned within the container. The anode comprises a base material selected from titanium and niobium. An outer layer of platinum is bonded to the base. The anode comprises a cylindrical shape. The cathode is also connected to the power supply and comprises titanium and has a substantially cylindrical shape. The cathode is positioned concentrically in relation to the anode. The spacing between the cathode and the anode is not greater than a preferred amount. Moreover, the voltage potential between the cathode and the anode is not greater than a preferred amount.

Finally, and most closely related to the present invention, U.S. Pat. No. 6,296,744 to Djeiranishvili et al, teaches an apparatus for the electrochemical treatment of a liquid medium. The apparatus contains at least one midstream electrolytic cell with unipolar electrodes of positive and negative polarity, which are connected to a source of continuous electrical current and positioned on opposite sides of a semipermeable diaphragm or membrane which divides the cell into anode and cathode electrode chambers. The chambers have pipelines attached to their nozzles. The pipelines include a feed pipe for the liquid medium being treated, a cathodic outlet pipe with a discharge point for carrying the liquid medium away from the cathode chamber, an anode outlet pipe for carrying the liquid medium from the anode chamber into the catalytic reactor for breaking down active chlorine, an exit line connected to the reactor, and a discharge point for carrying the liquid medium away to the place of collection.

While it is well known to utilize an ion selective barrier between the anode and cathode chambers of an electrolysis unit, to date it is not known to provide a supply of flowing ionic solutions in a chamber intermediate the anode and cathode chambers to facilitate the production of oxidative reduction potential (ORP) water.

DISCLOSURE OF INVENTION

The method and apparatus for producing ORP water of the present invention provides a more effective, efficient, and economical means for electrolytically producing oxidation reduction potential water from aqueous salt solutions for use in disinfection, sterilization, decontamination, wound cleansing, and the like. It accomplishes this objective by providing an electrolysis unit having a novel three compartment cell comprising a cathode chamber, an anode chamber, and a saline solution chamber interposed therebetween. Two communicating membranes separate the three chambers. The center chamber include a fluid flow inlet and outlet and contains insulative material that ensures direct voltage potential does not travel through the chamber. A supply of water flows through the cathode and anode chambers at the respective sides of the saline chamber. Saline solution flows through the center chamber, either by circulating a pre-prepared aqueous solution containing ionic species, or, alternatively, by circulating pure water or an aqueous solution of, e.g., aqueous hydrogen chloride and ammonium hydroxide, over particulate insulative material coated with a solid electrolyte. Electrical current is provided to the communicating membranes separating the chambers, thus causing an electrolytic reaction that produces both oxidative (positive) and reductive (negative) ORP water having pH levels ranging from approximately 8 to 12. The reductive water is dispensed into a collecting chamber main tank that contains inert atmosphere (preferably nitrogen), an ultrasonic agitation system, and an inductive heater. the oxidative water is drained to a second storage chamber.

Reductive water in the main tank can be utilized to disinfect and decontaminate articles or can be packaged and provided for shipping for use by hospitals, medical device companies, or other interests having strict sanitation protocols. The oxidative water can be used in such diverse applications as an insecticide in organic farming or in the fabrication of microchips and integrated circuit boards.

Note: As used herein and in the attached drawings, ORP water is used interchangeably with electrolyzed (EW) water.

BRIEF DESCRIPTION OF THE DRAWINGS

FIG. 1 is a schematic diagram of the essential components of the apparatus for producing negative and positive oxidative reductive potential (ORP) water of the present invention;

FIG. 2 is schematic diagram showing the inventive system using tap water as a water source and including a switching regulator and controller;

FIG. 3 illustrates the electrolytic cell and the electrolytic species generated in the reaction when the inventive system is used to electrolyze pure water passed through particulate insulative material coated with, or porous solid electrolyte;

FIG. 4 illustrates the electrolytic species generated in the reaction when the inventive system is used to electrolyze aqueous hydrogen chloride and ammonium hydroxide;

FIG. 5 illustrates the properties of ORP water produced by the inventive apparatus; and FIG. 6 shows the stability of ORP water as a function of the cell type in which it is produced.

BEST MODE FOR CARRYING OUT THE INVENTION

Referring to FIGS. 1 through 6, wherein like reference numerals refer to like components in the various views, FIG. 1 is a schematic diagram of the inventive apparatus for producing positive and negative ORP water of the present invention. This view shows that the inventive device, generally denominated 10, comprises a unique electrolysis system which utilizes a three-chambered electrolysis unit or cell specifically adapted for producing ORP water. The system includes a water inlet tank 12 in fluid communication with an electrolysis unit 14 having an anode chamber 16, a cathode chamber 18, and a saline solution chamber 20 interposed between the anode and cathode chambers.

Referring now to FIGS. 1, 3 and 4, the three chambers of the electrolysis unit are enclosed in a housing 22 in which are inserted a metal anode electrode membrane 24 facing the anode chamber, a first ion exchange membrane 25 approximated or mated to the anode electrode and separating the anode chamber from the saline solution chamber, a metal cathode electrode membrane 26, and a second ion exchange membrane 27 mated to the cathode electrode and separating the cathode chamber from the saline solution chamber. The metal electrodes are preferably generally planar, are approximated surface-to-surface with the ion exchange membranes, and generally match the cross-sectional surface area of the ion exchange membranes. However, the electrodes include a plurality of passages or apertures or are otherwise configured to expose a substantial portion of the surface of the ion exchange membranes to the fluid in their respective chambers.

The saline solution chamber includes a particulate insulating material (preferably ceramic), which permits the flow of solution through the saline chamber in an amount of at least 10 L/min., but prevents a direct voltage potential from traveling between the two membranes or the migration of ionic species between the anode and cathode chambers. However, the conductive metal electrode and ion exchange membranes separating the chambers are permeable enough to allow ionic species to travel between the saline solution chamber and the respective cathode and anode chambers.

Pure, ultrapure, or deionized water is pumped from tank 12 via pump 13 to the anode chamber through anode water inlet line 15a, and to the cathode chamber through cathode water inlet line 17a. (The term "line", as used herein, signifies tubes, pipes, and/or pipelines suitable for conveying liquids and gases). The water supply from tank 12 may consist of distilled, purified, or ultra pure water. Flow rate to each of the chambers is regulated by flow meters 19, 21. As an alternative, illustrated in FIG. 2, the water source may be a conventional tap supply 12'.

A source of electrical potential 23 is connected to the anode and cathode metal membranes 24, 26 so as to induce an anodic oxidation reaction in the anode chamber 16 and a cathodic reduction reaction in the cathode chamber 18. The resulting oxidative (positive ORP) water and reductive (negative ORP) water are directed from the electrolysis unit, the former flowing through anode outlet line 15b and the latter through cathode outlet line 17b. The reductive/negative ORP water is conveyed to a main tank 28, and thereafter made available for such diverse uses as decontamination, disinfection, sterilization, anti-microbial cleansing, wound cleansing, and the like. The positive/oxidative ORP water is sent, via drain 30, to another storage tank 42 (FIG. 2) for various other uses, including use as an insecticide or pesticide in organic farming, or as a cleanser in electronics fabrication. To promote stability and long shelf life, the main tank is provided with an inert atmosphere (preferably nitrogen) from a gas supply 38, which preferably passes through a gas heater 40 before introduction into the tank. The main tank also includes an ultrasonic agitation system and an inductive heater, which are not shown but which are well known in the art.

During electrolysis the saline solution (preferably aqueous NaCl) is pumped by a mid-pump 33 in a cyclic flow from a middle tank 32, through an intermediate inlet line 21a, the saline solution chamber 20, and then back through an intermediate outlet line 21b to the middle tank 32.

After collection in main tank 28, ORP water can be recycled for successive processing after circulation through a high pH buffer tank 34 and one or an array of particulate filters 36 on a buffer line 37 connecting the buffer tank to the electrolytic unit. The line preferably includes a buffer pump 39. Alternatively, pure water or an aqueous solution may be circulated through the saline solution chamber and passed through a porous, solid electrolyte contained therein to form an aqueous solution containing ionic species (see FIGS. 3 and 4). The solid electrolyte may be provided as a coating on particulate insulative material, such as glass or porcelain.

Gate valves, S/V1 through S/V10, are positioned along the fluid lines as appropriate for the regulation of fluid flow into, to, and through the tanks, filters, and electrolytic cell.

The flow rate of each electrolyzed water may be varied but is preferably between 1.0 L/min. to 20 L/min, depending on the capacity of the device.

Summarily, and as illustrated most generally in FIGS. 1 and 2, the inventive apparatus for producing negative and positive oxidative and reductive potential (ORP) water of the present invention comprises a water supply, a novel three-compartment electrolytic cell, a saline solution fluid circuit, an electric current source, an ORP water collection tank, and a control circuit. The cell for producing electrolyzed water includes an anode compartment, an intermediate (saline solution) compartment, and a cathode compartment. Pure water or tap water is passed through an anode compartment and a cathode compartment. A flowing aqueous solution of NaCl is provided within an intermediate compartment; or, alternatively, water or an aqueous solution is conveyed through the intermediate compartment and over particulate insulative material and an ionic compound, either deposited on the insulative material or in an uncombined particulate form. The three-compartment cell is adapted for the efficient production of a highly oxidative solution and a highly reductive solution while the concentration of aqueous solution is reduced.

The system flows are divided into two groups depending on the control processes. In the system depicted in FIG. 2, the polarity of the electrodes is fixed. However, as an alternative, oxidative water and reductive water may be automatically changed by reversing the polarity of electrodes. Sterilization efficiency is improved by washing with reductive and alkaline water is prior to washing with acidic and oxidative water.

A controller 52 is installed to control fluid flow throughout the electrolytic system, and a compact switching regulator 54 is incorporated into the device as an electric source. Flow sensors 44, pH sensors 46, ORP sensors 48, and level sensors 50, in electronic communication with the controller, can be incorporated according to customer preferences. In this system, a washing device is not included.

The inventive apparatus produces two types of water by electrolyzing pure water or tap water: Firstly, acidic and oxidative water; pH-3, ORP>1100 mV (vs., Ag/AgCI); and secondly, alkaline and reductive water; pH 11-12, ORP<−800 mV. ISO single exposure ocular and skin irritation studies in rabbits show that ORP water having a pH of 12.44 is not an irritant to the ocular or dermal tissue of a rabbit.

Referring now to FIG. 5, a graph 60 which illustrates the properties of ORP water produced by the inventive apparatus, it will be appreciated that both the oxidative and the reductive ORP water produced by the inventive system have industrially applicable properties. Positive ORP (anode) water 62 produced through the use of a supporting electrolyte and having a pH of between 1.0 and 6.0 and an ORP between 0.75 and 1.5 $V_{cs}$ NHE may be employed for metal and organic contaminant removal, surface oxidation, and sterilization. Anode water 64 produced through the electrolysis of deionized water and having a pH of between 5 and 7 and an ORP of between 0.75 and 1.25 may be employed to prevent metal contamination, organic contaminant removal, surface oxidation, and sterilization. Negative ORP (cathode) water 66 produced in the inventive system with a supporting electrolyte and having a pH of between 4 and 14 and an ORP of between 0.0 and −1.25 is useful for particle removal and the prevention of surface oxidation. Cathode water 68 produced using deionized water and having a pH of between 6 and 8 and an ORP of between 0.25 and 0.75 may be usefully employed to prevent particle contamination and surface oxidation.

FIG. 6 is a chart 70 showing the stability of ORP water as a function of the cell type in which it is produced.

Specification for ORP Water Apparatus

A specification for a preferred embodiment of the inventive apparatus is as follows:

a. Electrolyzed Water Supply Line Specifications

| flow rate max. | 5 L/min. |
|---|---|
| temperature | less than 40° C. |
| pressure | 0.2 Mpa | b. Middle Compartment Solution Line Specifications

| flow rate max. | 5 L/min. |
|---|---|
| temperature | less than 40° C. |
| pressure | 0.05 Mpa | c. Measurements

| pH | 1~14 |
|---|---|
| ORP | 1999~−1999 mV |
| flow rate | 1~5 |

Specification of Components

Electrolysis devices are divided into types depending upon the flow rate of electrolyzed water: Flow rates of 1, 2, and 4 liters per minute are commonly available. The three compartment cells contained in the embodiments of the inventive apparatus are divided into TYPE A and TYPE B cells. TYPE A cells are suitable for producing electrolyzed water at a flow rate of one L/min. TYPE B cells are suitable for electrolyzing at a flow rate of two L/min. The flow rates of two and four L/min. are made possible by a parallel combination of TYPE A and TYPE B cells.

In order to produce electrolyzed water at constant pH and ORP, the electrolysis current must be kept constant. In general, only voltage is controllable when using switching regulators. However, an MCS-1 may be provided. This is a special current-controlled switching regulator. Moreover, the electrolysis current can be regulated by a microcomputer control.

The specifications of these devices are summarized in Table 1.

TABLE 1

SUMMARY OF SPECIFICATIONS

| No | Type of Cell | No. of Cell | Flow Rate | Current | Voltage | Electric Source | Type of PCB | Current Control |
|---|---|---|---|---|---|---|---|---|
| 1 | Type A | 1 | 1 | 10 | 15 | HK-150A | Small | None |
| 2 | Type A | 1 | 1 | 10 | 17 | MCS-1 | Small | Possible |
| 3 | Type A | 1 | 1 | 10 | 17 | MCS-1 | Large | Possible |
| 4 | Type A | 2 | 2 | 10 | 15 | HK-150A * 2 | Small | None |
| 5 | Type A | 2 | 2 | 10 | 17 | MCS-1 * 2 | Small | Possible |
| 6 | Type A | 2 | 2 | 10 | 17 | MCS-1 * 2 | Large | Possible |
| 7 | Type A | 2 | 2 | 13 | 24 | RWS300A | Large | Possible |
| 8 | Type B | 1 | 2 | 21 | 15 | RWS300A | Large | Possible |
| 9 | Type B | 2 | 4 | 24 | 28 | SR660 | Large | Possible |
| 10 | Type B | 2 | 4 | 21 | 15 | RWS300A * 2 | Large | Possible |

FIGS. 1, 2 and 3, are schematic diagrams of the system configuration of the inventive apparatus. The arrangement of structural and operative components can be described as follows:

(1) Case

| dimension | 270 × 350 × 300 mm |
|---|---|
| material | SUS304 |

(2) Cell
a. TYPE A

| | |
|---|---|
| number | 1 or 2 |
| structure | 3 compartment type |
| electrode | |
| area | 60 × 80 mm |
| material platinum | plated titanium + platinum mesh |
| frame | |
| material | PVC |
| temperature | Max. 45° C. |
| pressure | 0.2 Mpa |
| conditions of electrolysis | |
| inlet water | |
| anode | pure water, tap water |
| cathode | pure water, tap water |
| middle | electrolyte solution, saturated NaCl solution |
| flow rate | usually 1 L/min. |
| electrolysis current | Max. 10 A | b. TYPE B

| | |
|---|---|
| number | 1 or 2 |
| structure | 3 compartment type |
| electrode | |
| area | 60 × 160 mm |
| material | platinum plated titanium + platinum mesh |
| frame | |
| material | PVC |
| temperature | Max. 45° C. |
| pressure | 0.2 Mpa |
| conditions of electrolysis | |
| inlet water | |
| anode | pure water, tap water |
| cathode | pure water, tap water |
| middle | electrolyte solution saturated NaCl solution\ |
| flow rate | usually 2 L/min. |
| electrolysis current | Max. 20 A |

(3) Middle Compartment Tank

| | |
|---|---|
| number | 1 |
| volume | 2 L |
| material | PE |

(4) Circulation Pump

| | |
|---|---|
| number | 1 |
| input | AC 100 V 3 W |
| output | 1.5 m 3.5 L/min. |

(5) Switching Regulator
Four models of switching regulator may be employed.
a. HK-150

| | |
|---|---|
| input | AC 100 V 320 W |
| output | DC 15 V 10 A | b. MCS-1

| | |
|---|---|
| input | AC 100 V |
| output | DC 17 V 11 A current control | c. RWS200A

| | |
|---|---|
| input | AC 100 V 400 W |
| output | DC 15 V 21 A (controllable by micro-computer) | d. SR660C

| | |
|---|---|
| input | AC 100 V 1600 W |
| output | DC 28 V 24 A (controllable by micro-computer) |

(6) Control Panel (Print Circuit Board)
Two models of control panels are available: Small PCB and Large PCB.
a. Function of Small PCB (the control panel is shown in FIG. 4)

| | |
|---|---|
| operation | start to electrolyze/Stop to electrolyze |
| display | electrolysis current, electrolysis voltage, pH, ORP, flow rate |
| safety | |
| electrolysis current | high and low |
| level of middle compartment tank | low temperature in the case high flow rate low | b. Function of Large PCB (control panel shown in FIG. 5)

| | |
|---|---|
| operation | start electrolysis/stop electrolysis; automatically wash (sterilize); selection of reduction/oxidation water; stop to pass water through device; start to pass water through device; adjust the washing time |
| display | |
| anode | pH |
| | ORP |
| | flow rate |
| cathode | pH |
| | ORP |
| | flow rate |
| safety | |
| electrolysis current | high and low |
| level of middle comp. tank | low |
| level of washing tank | low |
| concentration of hydrogen | high |
| flow rate | low |
| temperature | high |

While the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Accordingly, the proper scope of the present invention should be determined only by the broadest interpretation of the appended claims so as to encompass all such modifications as well as all relationships equivalent to those illustrated in the drawings and described in the specification.

What is claimed as invention is:

1. A method of producing negative and positive oxidative reductive potential (ORP) water, comprising the steps of:
   (a) providing a three-chambered electrolysis unit having an anode chamber, a cathode chamber, and a saline solution chamber interposed between said anode and cathode chambers, wherein the anode chamber is separated from the saline solution chamber by a metal anode electrode and a first ion exchange membrane, wherein the cathode chamber is separated from the saline solution chamber by a metal cathode electrode and a second ion exchange membrane, and wherein the saline solution chamber includes a particulate insulating material;
   (b) providing a flow of water to and through the anode and cathode chambers from at least one water supply in fluid communication with the anode and cathode chambers;
   (c) providing a circulating fluid flow of saline solution to and through the saline solution chamber from at least one fluid supply, wherein the flow of saline solution through the saline solution chamber is at least about 10 L/min;
   (d) simultaneously with steps (b) and (c), providing electrical current to the anode and cathode electrodes from a source of electrical potential connected to the anode electrode and the cathode electrode; and
   collecting ORP water produced by the electrolytic reaction in the electrolysis unit, wherein the negative ORP water from the cathode chamber has a pH of between 6 and 8.

2. The method of claim 1, wherein said negative ORP water has an ORP between 0.25 and 0.75 $V_{cs}$ NHE.

* * * * *

UNITED STATES PATENT AND TRADEMARK OFFICE
CERTIFICATE OF CORRECTION

| | | |
|---|---|---|
| PATENT NO. | : 8,062,500 B2 | Page 1 of 1 |
| APPLICATION NO. | : 10/496092 | |
| DATED | : November 22, 2011 | |
| INVENTOR(S) | : Osao Sumita | |

It is certified that error appears in the above-identified patent and that said Letters Patent is hereby corrected as shown below:

On the face of the patent, please add the following indications:

(60)     Related U.S. Application Data

U.S. 60/338,376                Dec. 5, 2001

Signed and Sealed this
Seventeenth Day of January, 2012

David J. Kappos
*Director of the United States Patent and Trademark Office*